US010624986B2

(12) United States Patent
Lu et al.

(10) Patent No.: US 10,624,986 B2
(45) Date of Patent: Apr. 21, 2020

(54) ABSORBENT MATERIALS, PRODUCTS INCLUDING ABSORBENT MATERIALS, COMPOSITIONS, AND METHODS OF MAKING ABSORBENT MATERIALS

(71) Applicant: KEMIRA OYJ, Helsinki (FI)

(72) Inventors: Chen Lu, Marietta, GA (US); Vladimir Grigoriev, Cologne (DE); Scott Rosencrance, Douglasville, GA (US); Henry Skoog, Roswell, GA (US)

(73) Assignee: KEMIRA OYJ, Helsinki (FI)

( * ) Notice: Subject to any disclaimer, the term of this patent is extended or adjusted under 35 U.S.C. 154(b) by 738 days.

(21) Appl. No.: 14/431,409

(22) PCT Filed: Sep. 5, 2013

(86) PCT No.: PCT/IB2013/002636
§ 371 (c)(1),
(2) Date: Mar. 26, 2015

(87) PCT Pub. No.: WO2014/049437
PCT Pub. Date: Apr. 3, 2014

(65) Prior Publication Data
US 2015/0238650 A1    Aug. 27, 2015

Related U.S. Application Data

(60) Provisional application No. 61/705,703, filed on Sep. 26, 2012.

(51) Int. Cl.
| | | |
|---|---|---|
| *A61L 15/60* | (2006.01) | |
| *A61L 15/22* | (2006.01) | |
| *B01J 20/26* | (2006.01) | |
| *B01J 20/28* | (2006.01) | |

(52) U.S. Cl.
CPC .............. *A61L 15/60* (2013.01); *A61L 15/225* (2013.01); *B01J 20/267* (2013.01); *B01J 20/28038* (2013.01); *Y10T 442/20* (2015.04)

(58) Field of Classification Search
CPC ........ A61L 15/60; A61L 15/225; A61L 15/26; B01J 20/28038; B01J 20/267; D21H 17/37; D21H 17/002; D21H 17/56; D21H 17/55; Y10T 442/20
See application file for complete search history.

(56) References Cited

U.S. PATENT DOCUMENTS

| | | | | |
|---|---|---|---|---|
| 2,926,116 A | * | 2/1960 | Keim ................... | C08G 69/48 162/164.3 |
| 4,319,019 A | * | 3/1982 | Lehmann .............. | C08G 69/48 162/168.5 |
| 4,689,374 A | * | 8/1987 | Hansson ............... | D21H 17/55 162/164.3 |
| 5,614,597 A | * | 3/1997 | Bower ............... | C08G 73/0286 525/430 |
| 5,972,691 A | * | 10/1999 | Bates ................... | C08G 73/022 162/100 |
| 6,077,394 A | | 6/2000 | Spence et al. | |
| 6,429,267 B1 | * | 8/2002 | Riehle .................. | C08G 73/02 162/164.1 |
| 6,936,136 B2 | | 8/2005 | Shannon et al. | |
| 7,175,740 B2 | * | 2/2007 | Riehle ................. | C08G 73/022 162/164.3 |
| 2002/0115969 A1 | * | 8/2002 | Maeda ............. | A61F 13/15658 604/368 |
| 2003/0069359 A1 | * | 4/2003 | Torii ..................... | A61F 13/531 525/178 |
| 2006/0173434 A1 | * | 8/2006 | Zoromski .............. | A61F 13/53 604/374 |
| 2009/0133846 A1 | * | 5/2009 | Grigoriev .............. | C08L 79/02 162/112 |
| 2010/0270501 A1 | * | 10/2010 | Torii ....................... | C08L 33/02 252/194 |
| 2012/0247697 A1 | * | 10/2012 | Lu ....................... | C08G 73/0286 162/111 |
| 2013/0160959 A1 | * | 6/2013 | Rosencrance .......... | D21H 17/56 162/164.6 |

FOREIGN PATENT DOCUMENTS

| | | |
|---|---|---|
| CN | 101541862 A | 9/2009 |
| CN | 102191720 A | 9/2011 |
| GB | 2141130 A | 12/1984 |
| KR | 10-0573946 B1 | 4/2006 |
| WO | 9832798 | 7/1998 |
| WO | 2007008945 A1 | 1/2007 |
| WO | 2008089419 | 7/2008 |
| WO | 2008089419 A1 | 7/2008 |
| WO | 2012135455 A1 | 10/2012 |

(Continued)

OTHER PUBLICATIONS

Translation of the Search Report from CN Application No. 201380061617.8 dated Aug. 31, 2016.
Search Report from CN Application No. 201380061617.8 dated May 12, 2017.
International Search Report dated Feb. 5, 2014.
Chinese Search Report, Application No. 201380061617.8; 2 pages. Translation also attached.

*Primary Examiner* — Michael Zhang
(74) *Attorney, Agent, or Firm* — Berggren LLP

(57) ABSTRACT

In various exemplary embodiments described herein, an absorbent structure (e.g., a paper material) having an applied absorbent material (e.g., an absorbent film) may be formed by treating a fiber (e.g., a cellulosic fiber) with an applied absorbent material forming system (also referred to as a "film forming system"), absorbent materials, compositions, methods of making absorbent materials, and the like.

16 Claims, No Drawings

(56) References Cited

FOREIGN PATENT DOCUMENTS

| WO | 2013046060 A1 | 4/2013 |
| WO | 2013095952 A1 | 6/2013 |
| WO | 2013179139 A1 | 12/2013 |

* cited by examiner

ABSORBENT MATERIALS, PRODUCTS INCLUDING ABSORBENT MATERIALS, COMPOSITIONS, AND METHODS OF MAKING ABSORBENT MATERIALS

CROSS-REFERENCE TO RELATED APPLICATION

This application is the 35 U.S.C. § 371 national stage application of PCT Application No. PCT/IB2013/002636, filed Sep. 5, 2013, the entirety of which is hereby incorporated by reference and which also claims priority to, and the benefit of, U.S. provisional application entitled "Absorbent Materials, Products Including Absorbent Materials, Compositions, and Methods of Making Absorbent Materials" having Ser. No. 61/705,703, filed on Sep. 26, 2012, the entirety of which is hereby incorporated by reference.

BACKGROUND

An important characteristic of paper products is the ability to absorb fluid, in particle, aqueous solutions. Paper products should not be overly expensive or provide chemicals that can have adverse effects on those using the products. Although some paper products achieve one or more of these goals, there is still a need to find alternatives to the products currently being commercialized.

SUMMARY

In various exemplary embodiments described herein, an absorbent structure (e.g., a paper material) having an applied absorbent material (e.g., an absorbent film) may be formed by treating a fiber (e.g., a cellulosic fiber) with an applied absorbent material forming system (also referred to as a "film forming system"), absorbent materials, compositions, methods of making absorbent materials, and the like.

At least one embodiment provides a structure that includes an absorbent structure having an applied absorbent material formed by a method comprising treating a fiber with an applied absorbent material forming system comprising a polyamine polyamidoamine epihalohydrin resin, wherein the applied absorbent material absorbs water at a ratio of about 10:1 or more of the dry polymer weight of the polyamine polyamidoamine epihalohydrin resin.

At least one embodiment provides a method of making an absorbent structure that includes: introducing to a fiber an applied absorbent material forming system comprising a polyamine polyamidoamine epihalohydrin resin.

At least one embodiment provides an absorbent structure having an applied absorbent material formed by a method comprising treating a fiber with an applied absorbent material forming system comprising a blend of two or more polymers, wherein at least one first polymer is self-crosslinking and reactive towards one of the other polymers in the blend, and at least a second polymer that reacts with the first polymer, wherein the applied absorbent material absorbs water at a ratio of about 10:1 or more, of the dry polymer weight of the blend.

At least one embodiment provides a method of making an absorbent structure that includes introducing to a fiber an applied absorbent material forming system comprising a blend of two or more polymers, wherein at least one first polymer is self-crosslinking and reactive towards one of the other polymers in the blend, and at least a second polymer that reacts with the first polymer, wherein the film absorbs water at a ratio of about 10:1 or more, of the dry polymer weight of blend.

At least one embodiment provides a composition that is a mixture of a blend of two or more polymers, wherein at least one first polymer is self-crosslinking and reactive towards one of the other polymers in the blend, and at least a second polymer that reacts with the first polymer, wherein the mixture in the form of an applied absorbent material absorbs water at a ratio of about 10:1 or more, of the dry polymer weight of the blend.

DETAILED DESCRIPTION OF THE EMBODIMENTS

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, paper chemistry, and the like, which are within the skill of the art. Such techniques are explained fully in the literature.

The examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms and phrases that shall be defined to have the following meanings unless a contrary intention is apparent.

Definitions

The term "substituted" refers to any one or more hydrogens on the designated atom or in a compound that can be replaced with a selection from the indicated group, provided that the designated atom's normal valence is not exceeded, and that the substitution results in a stable compound.

"Acrylamide monomer" refers to a monomer of formula: $H_2C=C(R_1)C(O)NR_2R_3$, where $R_1$ is H or $C_1$-$C_4$ alkyl, $R_2$ and $R_3$ are H, $C_1$-$C_4$ alkyl, aryl or arylalkyl. Exemplary acrylamide monomers include acrylamide and methacrylamide.

"Aldehyde" refers to a compound containing one or more aldehyde (—CHO) groups, where the aldehyde groups are capable of reacting with the amino or amido groups of a polymer comprising amino or amido groups as described herein. Exemplary aldehydes can include formaldehyde, paraformaldehyde, glutaraldehyde, glyoxal, and the like.

"Aliphatic group" refers to a saturated or unsaturated, linear or branched hydrocarbon group and encompasses alkyl, alkenyl, and alkynyl groups, for example.

"Alkyl" refers to a monovalent group derived from a straight or branched chain saturated hydrocarbon by the removal of a single hydrogen atom. Exemplary alkyl groups include methyl, ethyl, n- and iso-propyl, cetyl, and the like.

"Alkylene" refers to a divalent group derived from a straight or branched chain saturated hydrocarbon by the removal of two hydrogen atoms. Exemplary alkylene groups include methylene, ethylene, propylene, and the like.

"Amido group" and "amide" refer to a group of formula —C(O)NY$_1$Y$_2$, where Y$_1$ and Y$_2$ are independently selected from H, alkyl, alkylene, aryl and arylalkyl.

"Amino group" and "amine" refer to a group of formula —NY$_3$Y$_4$, where Y$_3$ and Y$_4$ are independently selected from H, alkyl, alkylene, aryl, and arylalkyl.

"Aryl" refers to an aromatic monocyclic or multicyclic ring system of about 6 to about 10 carbon atoms. The aryl is optionally substituted with one or more $C_1$-$C_{20}$ alkylene, alkoxy, or haloalkyl groups. Exemplary aryl groups include phenyl or naphthyl, or substituted phenyl or substituted naphthyl.

"Arylalkyl" refers to an aryl-alkylene-group, where aryl and alkylene are defined herein. Exemplary arylalkyl groups include benzyl, phenylethyl, phenylpropyl, 1-naphthylmethyl, and the like.

"Alkoxy" refers to an alkyl group as defined above with the indicated number of carbon atoms attached through an oxygen bridge. Exemplary alkoxy groups include methoxy, ethoxy, n-propoxy, i-propoxy, n-butoxy, s-butoxy, t-butoxy, n-pentoxy, and s-pentoxy.

"Halogen" refers to fluorine, chlorine, bromine, or iodine.

"Dicarboxylic acid compounds" includes organic aliphatic and aromatic (aryl) dicarboxylic acids and their corresponding acid chlorides, anhydrides and esters, and mixtures thereof. Exemplary dicarboxylic acid compounds include maleic acid, succinic acid, glutaric acid, adipic acid, pimelic acid, suberic acid, azelaic acid, sebasic acid, phthalic acid, isophthalic acid, terephthalic acid, naphthalenedicarboxylic acid, dimethyl maleate, dimethyl malonate, diethyl malonate, dimethyl succinate, di-isopropyl succinate, dimethyl glutarate, diethyl glutarate, dimethyl adipate, methyl ethyl adipate, dimethyl sebacate, dimethyl phthalate, dimethyl isophthalate, dimethyl terephthalate, dimethyl naphthalenedicarboxylate, dibasic esters (DBE), poly(ethylene glycol)bis(carboxymethyl)ether, succinyl chloride, glutaryl dichloride, adipoyl chloride, sebacoyl chloride, sebacate, phthaloyl chloride, isophthaloyl chloride, terephthaloyl chloride, naphthalenedicarboxylate, maleic anhydride, succinic anhydride, glutaric anhydride, phthalic anhydride, 1,8-naphthalic anhydride, and the like.

"Polyalkylene polyamine" can include polyamines such as polyethylene polyamine, polypropylene polyamine, and polyoxybutylene polyamine. In an embodiment, "polyalkylene polyamines" refers to those organic compounds having two primary amine (—NH$_2$) groups and at least one secondary amine group, where the amino nitrogen atoms are linked together by alkylene groups, provided no two nitrogen atoms are attached to the same carbon atoms. Exemplary polyalkylene polyamines include diethylenetriamine (DETA), triethylenetetramine (TETA), tetraethylenepentaamine (TEPA), dipropylenetriamine, and the like.

"Polyamidoamine" refers to a condensation product of one or more of the polycarboxylic acids and/or a polycarboxylic acid derivative with one or more of a polyalkylene polyamine.

"Polyvinylamine" and "polyvinylformamide/vinyl amine" can refer to a homopolymer or a copolymer of N-vinylformamide and/or N-vinylacetamide, where some mole % of the formyl or acetamide groups is hydrolyzed to form a polyvinylamine or polyvinylformamide/vinyl amine. The degree of hydrolysis may vary from about 1 to about 100 mole % or from about 5 to about 95 mole % or even about 10 to about 90 mole %. For example, commercial N-vinylformamide polymer is available in which 30 mole % of the formyl groups is hydrolyzed. Thus, the polyvinylamine may be a N-vinylformamide polymer, which has been hydrolyzed to give a polyvinylamine, where the mole % of amine will range from about 1 to about 100 mole %, about 10 to about 100 mole %, about 20 to about 100 mole %, about 30 to about 100 mole %, about 40 to about 95 mole %, or about 50 to about 95 mole %. In an embodiment, the hydrolysis reaction carried out on the N-vinylformamide is carried out by the action of acids, bases or enzymes by known methods. See for example, U.S. Pat. Nos. 4,421,602, 5,290,880 and 6,797,785, each of which is incorporated herein by reference. In an embodiment, the average molecular weight of the polyvinylamines (before glyoxalation) is, for example, from 1000 to 10 million, preferably from 10,000 to 5 million Daltons (determined by light scattering). This corresponds, for example, to K values of from 5 to 300, preferably from 10 to 250 (determined according to H. Fikentscher in 5% strength aqueous sodium chloride solution at 25° C. and at a polymer concentration of 0.5% by weight). In an embodiment, the polyvinylamine polymer may be linear crosslinked, chain-transferred, or crosslinked & chain-transferred (structured).

"Paper strength" means a property of a paper material, and can be expressed, inter alia, in terms of dry strength and/or wet strength. Dry strength is the tensile strength exhibited by the dry paper sheet, typically conditioned under uniform humidity and room temperature conditions prior to testing. Wet strength is the tensile strength exhibited by a paper sheet that has been wetted with water prior to testing.

"Nonwoven fabric" or "nonwoven web" refers to a web having a structure of individual fibers or threads that are interlaid, but not in a regular or identifiable manner as in a knitted fabric. Suitable fibers include natural and synthetic fibers, for example, cellulosic fibers, wood fibers of all varieties used in papermaking, non-woody fibers (e.g., bagasse, grasses, bamboo, and the like) and other plant fibers, such as cotton fibers, fibers derived from recycled paper; and the synthetic fibers, such as rayon, nylon, fiberglass, or polyolefin fibers. The formed product may be composed only of synthetic fibers. Natural fibers may be mixed with synthetic fibers. For instance, in the preparation of the product, material may be reinforced with synthetic fibers, such as nylon or fiberglass, or impregnated with nonfibrous materials, such as plastics, polymers, resins, or lotions. In an embodiment, nonwoven fabrics or webs can be formed from processes such as meltblowing processes, spunbonding processes, air laying processes, coform processes, foam formed processes, spunlace processes and bonded carded web processes. Nonwoven fabrics or webs ran also include cellulose fiber webs and other absorbent fiber webs formed using various processes, as well as apertured films having openings for passing liquid. The basis weight of nonwoven fabrics can be expressed in ounces of material per square yard (osy) or grams per square meter (gsm) and the fiber diameters useful are usually expressed in microns.

As used herein, the terms "paper" or "paper product" (these two terms can be used interchangeably herein) is understood to include a sheet material that contains paper fibers, which may also contain other materials. Suitable paper fibers include natural and synthetic fibers, for example, cellulosic fibers, wood fibers of all varieties used in papermaking, non-woody fibers (e.g., bagasse, grasses, bamboo, and the like) and other plant fibers, such as cotton fibers, fibers derived from recycled paper; and the synthetic fibers, such as rayon, nylon, fiberglass, or polyolefin fibers. The paper product may be composed only of synthetic fibers. Natural fibers may be mixed with synthetic fibers. For instance, in the preparation of the paper product, the paper web, or paper material may be reinforced with synthetic fibers, such as nylon or fiberglass, or impregnated with nonfibrous materials, such as plastics, polymers, resins, or lotions. As used herein, the terms "paper web" and "web" are understood to include both forming and formed paper sheet materials, papers, and paper materials containing paper fibers. The paper product may be a coated, laminated, or composite paper material. The paper product can be bleached or unbleached.

Paper can include, but is not limited to writing papers and printing papers (e.g., uncoated mechanical, total coated paper, coated free sheet, coated mechanical, uncoated free sheet, and the like), industrial papers, tissue papers of all varieties, paperboards, cardboards, packaging papers (e.g., unbleached kraft paper, bleached kraft paper), wrapping papers, paper adhesive tapes, paper bags, paper cloths, toweling, wipers, wallpapers, carpet backings, paper filters, paper mats, decorative papers, disposable linens and garments, and the like.

Paper can include tissue paper products. Tissue paper products include sanitary tissues, household tissues, industrial tissues, facial tissues, cosmetic tissues, soft tissues, absorbent tissues, medicated tissues, toilet papers, paper towels, paper napkins, paper cloths, paper linens, and the like. Common paper products include printing grade (e.g., newsprint, catalog, rotogravure, publication, banknote, document, bible, bond, ledger, stationery), industrial grade (e.g., bag, linerboard, corrugating medium, construction paper, greaseproof, glassine), and tissue grade (e.g., sanitary, toweling, condenser, wrapping).

In an exemplary embodiment, tissue paper may be a felt pressed tissue paper, a pattern densified tissue paper, or a high bulk, uncompacted tissue paper. In an exemplary embodiment, the tissue paper may be creped or uncreped, of a homogeneous or multilayered construction, layered or non-layered (blended), and one-ply, two-ply, or three or more plies. In an exemplary embodiment, tissue paper includes soft and absorbent paper tissue products that are consumer tissue products.

"Paperboard" is a paper that is thicker, heavier, and less flexible than conventional paper. Many hardwood and softwood tree species are used to produce paper pulp by mechanical and chemical processes that separate the fibers from the wood matrix. Paperboard can include, but is not limited to, semi-chemical paperboard, linerboards, containerboards, corrugated medium, folding boxboard, and cartonboards.

In an exemplary embodiment, paper refers to a paper product such as dry paper board, fine paper, towel, tissue, and newsprint products. Dry paper board applications include liner, corrugated medium, bleached, and unbleached dry paper board.

In an embodiment, paper can include carton board, container board, and special board/paper. Paper can include boxboard, folding boxboard, unbleached kraft board, recycled board, food packaging board, white lined chipboard, solid bleached board, solid unbleached board, liquid paper board, linerboard, corrugated board, core board, wallpaper base, plaster board, book bindery board, woodpulp board, sack board, coated board, gypsum board and the like.

"Pulp" refers to a fibrous cellulosic material. Suitable fibers for the production of the pulps are all conventional grades, for example mechanical pulp, bleached and unbleached chemical pulp, recycled pulp, and paper stocks obtained from all annuals. Mechanical pulp includes, for example, groundwood, thermomechanical pulp (TMP), chemothermochemical pulp (CTMP), groundwood pulp produced by pressurized grinding, semi-chemical pulp, high-yield chemical pulp and refiner mechanical pulp (RMP). Examples of suitable chemical pulps are sulfate, sulfite, and soda pulps. The unbleached chemical pulps, which are also referred to as unbleached kraft pulp, can be particularly used.

"Pulp slurry" refers to a mixture of pulp and water. The pulp slurry is prepared in practice using water, which can be partially or completely recycled from the paper machine. It can be either treated or untreated white water or a mixture of such water qualities. The pulp slurry may contain interfering substances (e.g., fillers). The filler content of paper may be up to about 40% by weight. Suitable fillers are, for example, clay, kaolin, natural and precipitated chalk, titanium dioxide, talc, calcium sulfate, barium sulfate, alumina, satin white or mixtures of the stated fillers.

"Papermaking process" is a method of making paper products from pulp comprising, inter alia, forming an aqueous pulp slurry that can include a cellulosic fiber, draining the pulp slurry to form a sheet, and drying the sheet. The steps of forming the papermaking furnish, draining, and drying may be carried out in any conventional manner generally known to those skilled in the art.

General Discussion

In various exemplary embodiments described herein, an absorbent structure (e.g., a paper material) having an applied absorbent material (e.g., an absorbent film) may be formed by treating a fiber (e.g., a cellulosic fiber) with an applied absorbent material forming system (also referred to as a "film forming system"). In an exemplary embodiment, the applied absorbent material absorbs water at a ratio of about 10:1 or more, about 20:1 or more, or about 30:1 or more, of the dry polymer weight of polymer(s) that forms the applied absorbent material.

In an embodiment, the absorbent structure can include a paper material and a nonwoven fabric or web. Although some reference may be made to a paper material or to a nonwoven fabric or web, the same teaching can be applied to other absorbent structures, and the teaching is not limited to the specific type of absorbent structure described.

In an embodiment, the applied absorbent material can include a film, a partial film, a coating, or the like. Although some reference may be made to a film, the same teaching can be applied to other applied absorbent materials, and the teaching is not limited to the specific type of applied absorbent material described.

In an embodiment, the applied absorbent material forming system can include a film forming system, a partial film forming system, a coating forming system, or the like. Although some reference may be made to a film forming system, the same teaching can be applied to other applied absorbent material forming systems, and the teaching is not limited to the specific type of applied absorbent material forming system described.

In an exemplary embodiment, the applied absorbent material forming system includes a polyamine polyamidoamine epihalohydrin resin. In another exemplary embodiment, the applied absorbent material forming system includes a blend of two or more polymers. In another exemplary embodiment, the applied absorbent material forming system includes a polyamine polyamidoamine epihalohydrin resin and a blend of two or more polymers. In an exemplary embodiment, the blend includes at least one first polymer that is self-crosslinking and reactive towards one of the other polymers in the blend, and at least a second polymer that reacts with the first polymer.

In an exemplary embodiment, the applied absorbent material forming system can be used to form an applied absorbent material on an absorbent structure such as a paper material. In an embodiment, the paper material can include paper towels, napkins, tissue, absorbent pads, diapers, feminine hygiene products, sanitary napkins, nonwoven material sheets and the like. In an exemplary embodiment, the applied absorbent material can be positioned anywhere (e.g., top, bottom, within, etc.) within the absorbent structure. In an exemplary embodiment, the applied absorbent material can be continuous throughout the absorbent structure and/or the absorbent structure can include a plurality of discrete areas (e.g., areas where more fluid is expected to be in contact with the absorbent structure) where the applied absorbent material is located within the paper material. The dimensions of the applied absorbent material can vary depending upon the type of paper material, use of the paper material, and the like. In an exemplary embodiment, the applied absorbent material can have a thickness of about 0.001 micrometers to 1000 micrometers or about 0.1 micrometers to 10 micrometers, which can be applied to the absorbent structure.

Now having described exemplary embodiments of the present disclosure in general, additional details regarding the components of the applied absorbent material forming system used to form the applied absorbent material are now discussed.

A) Polyamine Polyamidoamine Epihalohydrin Resin (PPAE)

As noted above, an exemplary embodiment of the applied absorbent material forming system can include PPAE. In an exemplary embodiment, PPAE resin can include, for example, those made using one or more processes as described in U.S. application Ser. No. 13/074,469 and filed on Mar. 29, 2011, which is incorporated herein by reference in its entirety. In an exemplary embodiment, the polyamine polyamidoamine epihalohydrin resin can be the reaction product of three components: a polyamine, a polyamidoamine, and an epihalohydrin. In an exemplary embodiment, either or both of the polyamidoamine and the polyamine can include a primary or a secondary amine that can react with epihalohydrin. The epihalohydrin can cross-link the polyamidoamine and the polyamine during the reaction to form the polyamine polyamidoamine epihalohydrin resin, resulting in a branched polymeric structure.

In an exemplary embodiment, the polyamine can include an ammonium, an aliphatic amine, an aromatic amine, or a polyalkylene polyamine. In an exemplary embodiment, the polyalkylene polyamine can include a polyethylene polyamine, a polypropylene polyamine, a polybutylene polyamine, a polypentylene polyamine, a polyoxylene polyamine, or a mixture thereof. In an exemplary embodiment, the polyamine can include ethylene diamine (EDA), diethylenetriamine (DETA), triethylenetetramine (TETA), tetraethylenepentamine (TEPA), dipropylenetriamine (DPTA), bishexamethylenetriamine (BHMT), N-methylbis (aminopropyl)amine (MBAPA), aminoethylpiperazine (AEP), pentaetehylenehexamine (PEHA), or a mixture thereof.

In an exemplary embodiment, the polyamidoamines can generally be prepared by reacting a polycarboxylic acid and/or a polycarboxylic acid derivative with one or more of the polyamines, such as, for example, those described above. The reactants may be heated to an elevated temperature, for example about 125 to 200° C. The reactants may be allowed to react for a predetermined time, for example about 1 to 10 hours. During the reaction, condensation water may be collected. The reaction may be allowed to proceed until the theoretical amount of water distillate is collected from the reaction. In an exemplary embodiment, the reaction may be conducted at atmospheric pressure.

In alternative embodiments, the reaction may proceed under a reduced pressure. Where a reduced pressure is employed, a lower temperature of about 75° C. to 180° C. may be utilized. At the end of this reaction, the resulting product may be dissolved in water at a concentration of about 20 to 90% by weight total polymer solids, or about 30 to 80% by weight total polymer solids, or about 40 to 70% by weight total polymer solids. In the preparation of the polyamidoamines, the molar ratio of the polyamine to the polycarboxylic acid and/or polycarboxylic acid derivative can be about 1.05 to 2.0.

In an exemplary embodiment, the polycarboxylic acid and/or polycarboxylic acid derivatives thereof (e.g., an ester of the polycarboxylic acid, an acid halide of the polycarboxylic acid, an acid anhydride of the polycarboxylic acid, and the like) can include malonic acid, glutaric acid, adipic acid, azelaic acid, citric acid, tricarballylic acid (1,2,3-propanetricarboxylic acid), 1,2,3,4-butanetetracarboxylic acid, nitrilotriacetic acid, N,N,N',N'-ethylenediaminetetraacetate, 1,2-cyclohexanedicarboxylic acid, 1,3-cyclohexanedicarboxylic acid, 1,4-cyclohexanedicarboxylic acid, phthalic acid, isophthalic acid, terephthalic acid, 1,2,4-benzenetricarboxylic acid (trimellitic acid), 1,2,4,5-benzenetetracarboxylic acid (pyromellitic acid), a carboxylate ester of any of these, an acid halide of any of these, an acid anhydride of any of these, or a mixture thereof.

In an exemplary embodiment, an ester of polycarboxylic acids can include dimethyl adipate, dimethyl malonate, diethyl malonate, dimethyl succinate, dimethyl glutarate and diethyl glutarate. In an exemplary embodiment, the acid anhydride can include succinic anhydride, maleic anhydride, N,N,N',N'-ethylenediaminetetraacetate dianhydride, phthalic anhydride, mellitic anhydride, pyromellitic anhydride, or a mixture thereof. In an exemplary embodiment, the acid halide can include adipoyl chloride, glutaryl chloride, sebacoyl chloride, or a mixture thereof.

In an exemplary embodiment, the polyamidoamine can have a molar ratio of polyalkylene polyamine to dicarboxylic acid of about 2:1 to 0.5:1, about 1.8:1 to 0.75:1, or about 1.6:1 to 0.85:1.

In an exemplary embodiment, the polyamidoamine resin can have a reduced specific viscosity of about 0.02 dL/g to 0.25 dL/g, about 0.04 dL/g to 0.20 dL/g, or about 0.06 dL/g to 0.18 dL/g. Reduced specific viscosity (RSV) can be measured using a glass capillary viscometer at 30° C. The efflux time of each sample can be determined three times and the average efflux time calculated. The RSV can be calculated using the following formula (1):

$$RSV = ((t - t_0))/(t_0 c) \quad (1)$$

where t is the average efflux time of the polyamidoamine sample diluted with 1 M NaCl solution, $t_0$ is the average efflux time of 1 M NaCl solution, c is the concentration of the diluted polyamidoamine sample, which is 5 g/dL.

In an exemplary embodiment, the epihalohydrin can be a difunctional crosslinker that is used to prepare the polyamine polyamidoamine epihalohydrin resin. In an exemplary embodiment, the epihalohydrin can include epichlorohydrin, epifluorohydrin, epibromohydrin, or epiiodohydrin, alkyl-substituted epihalohydrins, or a mixture thereof. In an exemplary embodiment, the difunctional crosslinker for preparing the polyamine polyamidoamine epihalohydrin resin is epichlorohydrin.

In an exemplary embodiment, the polyamine polyamidoamine epihalohydrin resin can generally be formed by reacting polyamine, polyamidoamine, and epihalohydrin, in an aqueous medium.

In an exemplary embodiment, the weight ratio of polyamine to polyamidoamine, can be about 1:100 to 100:1, about 1:50 to 50:1, or about 1:20 to 20:1. In an exemplary embodiment, the reaction temperature can be about 25 to 100° C., about 40 to 90° C., or about 50 to 80° C.

In an exemplary embodiment, the total solids of the polyamine polyamidoamine epihalohydrin resin can be about 5 to 80%, about 10 to 50%, or about 15 to 30%. In an exemplary embodiment, the pH values of the polyamine polyamidoamine epihalohydrin resin can be about 2 to 10, about 3 to 9, or about 3 to 8. In an exemplary embodiment, the weight average molecular weight of the polyamine polyamidoamine epihalohydrin resin can be about 350 Daltons (Da) to 10 million Da, about 1000 Da to 5 million Da, or about 5000 Da to 3 million Da. In an exemplary embodiment, the Brookfield viscosity of the polyamine polyamidoamine epihalohydrin resin can be about 3 to 1000 cps, about 5 to 500 cps, or about 8 to 300 cps, for a 20% by weight aqueous solution.

In an exemplary embodiment, the polyamine polyamidoamine epihalohydrin resin has an epihalohydrin/amine (also expressed herein as "epi/amine" or "E/N") ratio of about 0.8 or less, about 0.5 or less, about 0.45 or less, about 0.4 or less, or about 0.3 or less, where the lower limit can be about 0.01, about 0.001, or 0. The epi/amine ratio is calculated as the molar ratio of epichlorohydrin content to amine content. In an embodiment, the polyamine polyamidoamine epihalohydrin resin has an E/N ratio of about 0.01 to 0.8, about 0.01 to 0.5, about 0.01 to 0.45, about 0.01 to 0.4, or about 0.01 to 0.3.

B) Polymer Blend

As mentioned above, the applied absorbent material forming system can include a blend of polymers. In an exemplary embodiment, the applied absorbent material can be made using a blend of two or more polymers that can react with one another. In an exemplary embodiment, the polymer blend can include a self-crosslinking first polymer and a second polymer. In an exemplary embodiment, the self-crosslinking first polymer is self-crosslinking and reactive towards another polymer (e.g., the second polymer) present in the blend. In an exemplary embodiment, the second polymer is reactive with the self-crosslinking first polymer. In an exemplary embodiment, the ratio of the self-crosslinking first polymer and the second polymer can be about 1:99 to 99:1, 5:95 to 95:5 or about 10:90 to 90:10. Exemplary embodiments of the polymers that can be used in the polymer blend are described below.

B1) Self-Crosslinking First Polymer

In an exemplary embodiment, the self-crosslinking first polymer can include a self-crosslinking PAE, a self-crosslinking PPAE, a self-crosslinking aldehyde-functionalized polymer resin, or a combination thereof.

B1a) Self-Crosslinking PAE

In an exemplary embodiment, the self-crosslinking PAE can be prepared by reacting one or more polyalkylene polyamines and one or more dicarboxylic acid compounds to form a polyamidoamine and then reacting the polyamidoamine with epihalohydrin to form the polyamidoamine epihalohydrin resin. In various embodiments, the self-crosslinking PAE resin and the preparation of the self-crosslinking PAE resin may be as described in one or more of U.S. Pat. Nos. 2,926,116, 2,926,154, 3,197,427, 3,442,754, 3,311,594, 5,171,795, 5,614,597, 5,017,642, 5,019,606, 7,081,512, 7,175,740, 5,256,727, 5,510,004, 5,516,885, 6,554,961, 5,972,691, 6,342,580, and 7,932,349, and U.S. Published Patent Application 2008/0255320, each of which is incorporated herein by reference, where the self-crosslinking PAE resin functions and has the characteristics (e.g., total AOX level, azetidinium content, etc.) described herein, and the mixture produced using the self-crosslinking PAE resin functions and has the characteristics described herein.

In an exemplary embodiment, the epihalohydrin can include epichlorohydrin, epifluorohydrin, epibromohydrin, epiiodohydrin, alkyl-substituted epihalohydrins, or a mixture thereof. In one embodiment, the epihalohydrin is epichlorohydrin.

In an exemplary embodiment, the self-crosslinking PAE resin has an epihalohydrin/amine (also expressed herein as "epi/amine" or "E/N") ratio of about 0.8 or less, about 0.5 or less, about 0.45 or less, about 0.4 or less, or about 0.3 or less, where the lower limit can be about 0.1, about 0.01, or 0. In an embodiment, the self-crosslinking PAE resin has an E/N ratio of about 0.01 to 0.8, about 0.01 to 0.5, about 0.01 to 0.45, about 0.01 to 0.4, or about 0.01 to 0.3. The epi/amine ratio is calculated as the molar ratio of epichlorohydrin to amine content.

As mentioned above, the self-crosslinking PAE resin can be prepared by reacting epichlorohydrin with polyamidoamine. During the first step of the self-crosslinking PAE resin synthesis, epichlorohydrin reacts with polyamidoamine and forms amino-chlorohydrin. During the second step of the reaction, amino-chlorohydrin is converted azetidinium. In an exemplary embodiment, the azetidinium content can be controlled by selection of the polyamidoamine backbone, the percent solids content of the resin, ratio of the components to form the self-crosslinking PAE resin, the epihalohydrin/amine ratio, the time frame, temperature, and/or the pH of the reaction and/or addition of components, and the like. One or more of these variables can be used to produce a self-crosslinking PAE resin having an azetidinium content as described herein.

In an embodiment, the self-crosslinking PAE resin can have an azetidinium content of about 80% or less, of about 70% or less, of about 60% or less, of about 50% or less, or of about 40% or less. In an embodiment, the self-crosslinking PAE resin can have an azetidinium content of about 0.01 to 80%, about 0.01 to 70%, about 0.01 to 60%, about 0.01 to 50%, or about 0.01 to 40%.

Since all or a substantial portion of the epichlorohydrin is reacted with the amine groups to functionalize the polymer, the amount of epichlorohydrin that remains in the aqueous solution to react with water or chlorine to form byproducts is eliminated or substantially reduced as compared to when other commercially available components are used.

In an embodiment, the mixture can have a total level of epichlorohydrin and its byproducts (also noted as total absorbable organic halides (AOX) level) that can be about 400 ppm or less, about 300 ppm or less, about 200 ppm or less, about 100 ppm or less, about 50 ppm or less, or about 10 ppm or less, where the AOX level is based on 12.5% actives based total polymer solids. The AOX can include one or more of epihalohydrin, 1,3-dihalo-2-propanol, 3-monohalo-1,2-propanediol, and 2,3-dihalo-1-propanol. When the polyamidoamine epihalohydrin resin includes epichlorohydrin, the AOX can include one or more of epichlorohydrin, 1,3-dichloro-2-propanol, 3-monochloro-1,2-propanediol, and 2,3-dichloro-1-propanol. These compounds are known to be toxic to humans, so reduction or elimination of these components from paper is advantageous.

The phrase "% actives based" in regard to the mixture has a total level of epichlorohydrin and its byproducts means the total weight percentage of the epichlorohydrin and its byproducts in a product containing the specified percent weight of polymer actives. The % actives are measured as polymer solids by moisture balance.

B1b) Self-Crosslinking PPAE

In an exemplary embodiment, self-crosslinking PPAE resin can include, for example, those made using one or more processes as described in U.S. application Ser. No. 13/074,469 and filed on Mar. 29, 2011, which is incorporated herein by reference in its entirety. In an exemplary embodiment, the self-crosslinking PPAE resin can be the reaction product of three components: a polyamine, a polyamidoamine, and an epihalohydrin. In an exemplary embodiment, either or both of the polyamidoamine and the polyamine can include a primary or a secondary amine that can react with epihalohydrin. The epihalohydrin can crosslink the polyamidoamine and the polyamine during the reaction to form the self-crosslinking PPAE resin, resulting in a branched polymeric structure.

In an exemplary embodiment, the polyamine can include an ammonium, an aliphatic amine, an aromatic amine, or a polyalkylene polyamine. In an exemplary embodiment, the polyalkylene polyamine can include a polyethylene polyamine, a polypropylene polyamine, a polybutylene polyamine, a polypentylene polyamine, a polyhexylene polyamine, or a mixture thereof. In an exemplary embodiment, the polyamine can include ethylene diamine (EDA), diethylenetriamine (DETA), triethylenetetramine (TETA), tetraethylenepentamine (TEPA), dipropylenetriamine (DPTA), bishexamethylenetriamine (BHMT), N-methylbis(aminopropyl)amine (MBAPA), aminoethylpiperazine (AEP), pentaetehylenehexamine (PEHA), or a mixture thereof.

In an exemplary embodiment, the polyamidoamines can generally be prepared by reacting a polycarboxylic acid and/or a polycarboxylic acid derivative with one or more of the polyamines, such as, for example, those described above. The reactants may be heated to an elevated temperature, for example about 125 to 200° C. The reactants may be allowed to react for a predetermined time, for example about 1 to 10 hours. During the reaction, condensation water may be collected. The reaction may be allowed to proceed until the theoretical amount of water distillate is collected from the reaction. In an exemplary embodiment, the reaction may be conducted at atmospheric pressure.

In alternative embodiments, the reaction may proceed under a reduced pressure. Where a reduced pressure is employed, a lower temperature of about 75° C. to 180° C. may be utilized. At the end of this reaction, the resulting product may be dissolved in water at a concentration of about 20 to 90% by weight total polymer solids, or about 30 to 80% by weight total polymer solids, or about 40 to 70% by weight total polymer solids. In the preparation of the polyamidoamines, the molar ratio of the polyamine to the polycarboxylic acid and/or polycarboxylic acid derivative can be about 1.05 to 2.0.

In an exemplary embodiment, the polycarboxylic acid and/or polycarboxylic acid derivatives thereof (e.g., an ester of the polycarboxylic acid, an acid halide of the polycarboxylic acid, an acid anhydride of the polycarboxylic acid, and the like) can include malonic acid, glutaric acid, adipic acid, azelaic acid, citric acid, tricarballylic acid (1,2,3-propanetricarboxylic acid), 1,2,3,4-butanetetracarboxylic acid, nitrilotriacetic acid, N,N,N',N'-ethylenediaminetetraacetate, 1,2-cyclohexanedicarboxylic acid, 1,3-cyclohexanedicarboxylic acid, 1,4-cyclohexanedicarboxylic acid, phthalic acid, isophthalic acid, terephthalic acid, 1,2,4-benzenetricarboxylic acid (trimellitic acid), 1,2,4,5-benzenetetracarboxylic acid (pyromellitic acid), a carboxylate ester of any of these, an acid halide of any of these, an acid anhydride of any of these, or a mixture thereof.

In an exemplary embodiment, an ester of polycarboxylic acids can include dimethyl adipate, dimethyl malonate, diethyl malonate, dimethyl succinate, dimethyl glutarate and diethyl glutarate. In an exemplary embodiment, the acid anhydride can include succinic anhydride, maleic anhydride, N,N,N',N'-ethylenediaminetetraacetate dianhydride, phthalic anhydride, mellitic anhydride, pyromellitic anhydride, or a mixture thereof. In an exemplary embodiment, the acid halide can include adipoyl chloride, glutaryl chloride, sebacoyl chloride, or a mixture thereof.

In an exemplary embodiment, the polyamidoamine can have a molar ratio of polyalkylene polyamine to dicarboxylic acid of about 2:1 to 0.5:1, about 1.8:1 to 0.75:1, or about 1.6:1 to 0.85:1.

In an exemplary embodiment, the polyamidoamine resin can have a reduced specific viscosity of about 0.02 dL/g to 0.25 dL/g, about 0.04 dL/g to 0.20 dL/g, or about 0.06 dL/g to 0.18 dL/g. Reduced specific viscosity (RSV) can be measured using a glass capillary viscometer at 30° C. The efflux time of each sample can be determined three times and the average efflux time calculated. The RSV can be calculated using the following formula (1):

$$RSV = ((t-t_0))/(t_0 c) \quad (1)$$

where t is the average efflux time of the polyamidoamine sample diluted with 1 M NaCl solution, $t_0$ is the average efflux time of 1 M NaCl solution, c is the concentration of the diluted polyamidoamine sample, which is 5 g/dL.

In an exemplary embodiment, the epihalohydrin can be a difunctional crosslinker that is used to prepare the polyamine polyamidoamine epihalohydrin resin. In an exemplary embodiment, the epihalohydrin can include epichlorohydrin, epifluorohydrin, epibromohydrin, or epiiodohydrin, alkyl-substituted epihalohydrins, or a mixture thereof. In an exemplary embodiment, the difunctional crosslinker for preparing the self-crosslinking PPAE resin is epichlorohydrin.

In an exemplary embodiment, the self-crosslinking PPAE resin can generally be formed by reacting polyamine, polyamidoamine, and epihalohydrin, in an aqueous medium.

In an exemplary embodiment, the weight ratio of polyamine to polyamidoamine, can be about 1:100 to 100:1, about 1:50 to 50:1, or about 1:20 to 20:1. In an exemplary embodiment, the reaction temperature can be about 25 to 100° C., about 40 to 90° C., or about 50 to 80° C.

In an exemplary embodiment, the total solids of self-crosslinking PPAE resin can be about 5 to 80%, about 10 to 50%, or about 15 to 30%. In an exemplary embodiment, the pH values of the self-crosslinking PPAE resin can be about 2 to 10, about 3 to 9, or about 3 to 8. In an exemplary embodiment, the weight average molecular weight of self-crosslinking PPAE resin can be about 350 Daltons (Da) to 10 million Da, about 1000 Da to 5 million Da, or about 5000 Da to 3 million Da. In an exemplary embodiment, the Brookfield viscosity of the self-crosslinking PPAE resin can be about 3 to 1000 cps, about 5 to 500 cps, or about 8 to 300 cps, for a 20% by weight aqueous solution.

In an exemplary embodiment, the self-crosslinking PPAE resin has an epihalohydrin/amine (also expressed herein as "epi/amine" or "B/N") ratio of about 0.8 or less, about 0.5 or less, about 0.45 or less, about 0.4 or less, or about 0.3 or less, where the lower limit can be about 0.1, about 0.01, or 0. The epi/amine ratio is calculated as the molar ratio of epichlorohydrin content to amine content. In an embodiment, the self-crosslinking PPAE resin has an E/N ratio of about 0.01 to 0.8, about 0.01 to 0.5, about 0.01 to 0.45, about 0.01 to 0.4, or about 0.01 to 0.3.

B1c) Self-Crosslinking Aldehyde-Functionalized Polymer Resin

In an exemplary embodiment, the self-crosslinking aldehyde-functionalized polymer resin can be produced by reacting a polymer including one or more hydroxyl, amine, or amide groups with one or more aldehydes. In an exemplary embodiment, the self-crosslinking polymeric aldehyde-functionalized polymer resin can comprise gloxylated polyacrylamides, aldehyde-rich cellulose, aldehyde-functional polysaccharides, or aldehyde functional cationic, anionic or non-ionic starches. Exemplary materials include those disclosed in U.S. Pat. No. 4,129,722, which is herein incorporated by reference. An example of a commercially available soluble cationic aldehyde functional starch is Cobond® 1000 marketed by National Starch. Additional exemplary self-crosslinking aldehyde-functionalized polymers may include aldehyde polymers such as those disclosed in U.S. Pat. Nos. 5,085,736; 6,274,667; and 6,224,714; all of which are herein incorporated by reference, as well as the those of WO 00/43428 and the aldehyde functional cellulose described in WO 00/50462 A1 and WO 01/34903 A1. In an exemplary embodiment, the polymeric aldehyde-functional resins can have a molecular weight of about 10,000 Da or greater, about 100,000 Da or greater, or about 500,000 Da or greater. Alternatively, the self-crosslinking polymeric aldehyde-functionalized resins can have a molecular weight below about 200,000 Da, such as below about 60,000 Da.

In an exemplary embodiment, further examples of self-crosslinking aldehyde-functionalized polymers can include dialdehyde guar, aldehyde-functional wet strength additives further comprising carboxylic groups as disclosed in WO 01/83887, dialdehyde inulin, and the dialdehyde-modified anionic and amphoteric polyacrylamides of WO 00/11046, each of which are herein incorporated by reference. Another exemplary self-crosslinking aldehyde-functionalized polymer is an aldehyde-containing surfactant such as those disclosed in U.S. Pat. No. 6,306,249, which is incorporated herein by reference.

When used in an exemplary embodiment, the self-crosslinking aldehyde-functionalized polymer can have at least about 5 milliequivalents (meq) of aldehyde per 100 grams of polymer, more specifically at least about 10 meq, more specifically about 20 meq or greater, or most specifically about 25 meq, per 100 grams of polymer or greater.

In an exemplary embodiment, the polymeric self-crosslinking aldehyde-functionalized polymer can be a glyoxylated polyacrylamide, such as a cationic glyoxylated polyacrylamide as described in U.S. Pat. Nos. 3,556,932, 3,556,933, 4,605,702, 7,828,934, and U.S. Patent Application 20080308242, each of which are incorporated herein by reference. Such compounds include FENNOBOND™ 3000 and PAREZ™ 745 from Kemira Oyj of Helsinki, Finland, HERCOBOND™ 1366, manufactured by Hercules, Inc. of Wilmington, Del.

In an exemplary embodiment, the self-crosslinking aldehyde-functionalized polymer is a glyoxalated polyacrylamide resin having the ratio of the number of substituted glyoxal groups to the number of glyoxal-reactive amide groups being in excess of about 0.03:1, being in excess of about 0.10:1, or being in excess of about 0.15:1.

In an exemplary embodiment, the self-crosslinking aldehyde-functionalized polymer can be a glyoxalated polyacrylamide resin having a polyacrylamide backbone with a molar ratio of acrylamide to dimethyldiallylammonium chloride of about 99:1 to 50:50, about 98:1 to 60:40, or about 96:1 to 75:25. In an exemplary embodiment, the weight average molecular weight of the polyacrylamide backbone can be about 250,000 Da or less, about 150,000 Da or less, or about 100,000 Da or less. The Brookfield viscosity of the polyacrylamide backbone can be about 10 to 10,000 cps, about 25 to 5000 cps, about 50 to 2000 cps, for a 40% by weight aqueous solution.

B2) Second Polymer

As noted above, the second polymer is reactive with the self-crosslinking first polymer. In exemplary embodiment, the second polymer can be a PAE, a PPAE, an aldehyde-functionalized polymer resin, a polyamidoamine crosslinked with dichloroethane, a polyvinylamine, a polyvinylformamide/vinyl amine, a polyamidoamine, polyethylenimine and polymers that can react with aldehydes such as polyvinyl alcohol, polyacrylamide, starch and its derivatives, carboxymethylcellulose, and the like.

B2a) PAE

In an exemplary embodiment, the PAE resin can be prepared by reacting one or more polyalkylene polyamines and one or more dicarboxylic acid compounds to form a polyamidoamine and then reacting the polyamidoamine with epihalohydrin to form the PAE resin. In various embodiments, the PAE resin and the preparation of the PAE resin may be as described in one or more of U.S. Pat. Nos. 2,926,116, 2,926,154, 3,197,427, 3,442,754, 3,311,594, 5,171,795, 5,614,597, 5,017,642, 5,019,606, 7,081,512, 7,175,740, 5,256,727, 5,510,004, 5,516,885, 6,554,961, 5,972,691, 6,342,580, and 7,932,349, and U.S. Published Patent Application 2008/0255320, each of which is incorporated herein by reference, where the PAE resin functions and has the characteristics (e.g., total AOX level, azetidinium content, etc.) described herein, and the mixture produced using the PAE resin functions and has the characteristics described herein.

In an exemplary embodiment, the epihalohydrin can include epichlorohydrin, epifluorohydrin, epibromohydrin, epiiodohydrin, alkyl-substituted epihalohydrins, or a mixture thereof. In one embodiment, the epihalohydrin is epichlorohydrin.

In an exemplary embodiment, the ratio of aldehyde-functionalized polymer resin to PAE resin can be about 1:1 to 100:1 or more or about 1:100 to 100:1.

In an exemplary embodiment, the PAE resin has an epihalohydrin/amine (also expressed herein as "epi/amine" or "E/N") ratio of about 0.8 or less, about 0.5 or less, about 0.45 or less, about 0.4 or less, or about 0.3 or less. In an embodiment, the PAE resin has an E/N ratio of about 0.01 to 0.8, about 0.01 to 0.5, about 0.01 to 0.45, about 0.01 to 0.4, or about 0.01 to 0.3. The epi/amine ratio is calculated as the molar ratio of epichlorohydrin to amine content.

As mentioned above, PAE resin can be prepared by reacting epichlorohydrin with polyamidoamine. During the first step of the PAE resin synthesis, epichlorohydrin reacts with polyamidoamine and forms amino-chlorohydrin. During the second step of the reaction, amino-chlorohydrin is converted azetidinium. In an exemplary embodiment, the azetidinium content can be controlled by selection of the polyamidoamine backbone, the percent solids content of the resin, ratio of the components to form the PAE resin, the epihalohydrin/amine ratio, the time frame, temperature, and/or the pH of the reaction and/or addition of components, and the like. One or more of these variables can be used to produce a PAE resin having an azetidinium content as described herein.

In an embodiment, the PAE resin can have an azetidinium content of about 80% or less, of about 70% or less, of about 60% or less, of about 50% or less, or of about 40% or less. In an embodiment, the ME resin can have an azetidinium content of about 0.01 to 80%, about 0.01 to 70%, about 0.01 to 60%, about 0.01 to 50%, or about 0.01 to 40%.

Since all or a substantial portion of the epichlorohydrin is reacted with the amine groups to functionalize the polymer, the amount of epichlorohydrin that remains in the aqueous solution to react with water or chlorine to form byproducts is eliminated or substantially reduced as compared to when other commercially available components are used.

In an embodiment, the mixture can have a total level of epichlorohydrin and its byproducts (also noted as total absorbable organic halides (AOX) level) that can be about 400 ppm or less, about 300 ppm or less, about 200 ppm or less, about 100 ppm or less, about 50 ppm or less, or about 10 ppm or less, where the AOX level is based on 12.5% actives based total polymer solids. The AOX can include one or more of epihalohydrin, 1,3-dihalo-2-propanol, 3-monohalo-1,2-propanediol, and 2,3-dihalo-1-propanol. When the polyamidoamine epihalohydrin resin includes epichlorohydrin, the AOX can include one or more of epichlorohydrin, 1,3-dichloro-2-propanol, 3-monochloro-1,2-propanediol, and 2,3-dichloro-1-propanol. These compounds are known to be toxic to humans, so reduction or elimination of these components from paper is advantageous.

The phrase "% actives based" in regard to the mixture has a total level of epichlorohydrin and its byproducts means the total weight percentage of the epichlorohydrin and its byproducts in a product containing the specified percent weight of polymer actives. The % actives are measured as polymer solids by moisture balance.

B2b) PPAE

In an exemplary embodiment, the PPAE resin can include, for example, those made using one or more processes as described in U.S. application Ser. No. 13/074,469 and filed on Mar. 29, 2011, which is incorporated herein by reference in its entirety. In an exemplary embodiment, the PPAE resin can be the reaction product of three components: a polyamine, a polyamidoamine, and an epihalohydrin. In an exemplary embodiment, either or both of the polyamidoamine and the polyamine can include a primary or a secondary amine that can react with epihalohydrin. The epihalohydrin can cross-link the polyamidoamine and the polyamine during the reaction to form the PPAE resin, resulting in a branched polymeric structure.

In an exemplary embodiment, the polyamine can include an ammonium, an aliphatic amine, an aromatic amine, or a polyalkylene polyamine. In an exemplary embodiment, the polyalkylene polyamine can include a polyethylene polyamine, a polypropylene polyamine, a polybutylene polyamine, a polypentylene polyamine, a polyhexylene polyamine, or a mixture thereof. In an exemplary embodiment, the polyamine can include ethylene diamine (EDA), diethylenetriamine (DETA), triethylenetetramine (TETA), tetraethylenepentamine (TEPA), dipropylenetriamine (DPTA), bishexamethylenetriamine (BHMT), N-methylbis (aminopropyl)amine (MBAPA), aminoethylpiperazine (AEP), pentaetehylenehexamine (PEHA), or a mixture thereof.

In an exemplary embodiment, the polyamidoamines can generally be prepared by reacting a polycarboxylic acid and/or a polycarboxylic acid derivative with one or more of the polyamines, such as, for example, those described above. The reactants may be heated to an elevated temperature, for example about 125 to 200° C. The reactants may be allowed to react for a predetermined time, for example about 1 to 10 hours. During the reaction, condensation water may be collected. The reaction may be allowed to proceed until the theoretical amount of water distillate is collected from the reaction. In an exemplary embodiment, the reaction may be conducted at atmospheric pressure.

In alternative embodiments, the reaction may proceed under a reduced pressure. Where a reduced pressure is employed, a lower temperature of about 75° C. to 180° C. may be utilized. At the end of this reaction, the resulting product may be dissolved in water at a concentration of about 20 to 90% by weight total polymer solids, or about 30 to 80% by weight total polymer solids, or about 40 to 70% by weight total polymer solids. In the preparation of the polyamidoamines, the molar ratio of the polyamine to the polycarboxylic acid and/or polycarboxylic acid derivative can be about 1.05 to 2.0.

In an exemplary embodiment, the polycarboxylic acid and/or polycarboxylic acid derivatives thereof an ester of the polycarboxylic acid, an acid halide of the polycarboxylic acid, an acid anhydride of the polycarboxylic acid, and the like) can include malonic acid, glutaric acid, adipic acid, azelaic acid, citric acid, tricarballylic acid (1,2,3-propanetricarboxylic acid), 1,2,3,4-butanetetracarboxylic acid, nitrilotriacetic acid, N,N,N',N'-ethylenediaminetetraacetate, 1,2-cyclohexanedicarboxylic acid, 1,3-cyclohexanedicarboxylic acid, 1,4-cyclohexanedicarboxylic acid, phthalic acid, isophthalic acid, terephthalic acid, 1,2,4-benzenetricarboxylic acid (trimellitic acid), 1,2,4,5-benzenetetracarboxylic acid (pyromellitic acid), a carboxylate ester of any of these, an acid halide of any of these, an acid anhydride of any of these, or a mixture thereof.

In an exemplary embodiment, an ester of polycarboxylic acids can include dimethyl adipate, dimethyl malonate, diethyl malonate, dimethyl succinate, dimethyl glutarate and diethyl glutarate. In an exemplary embodiment, the acid anhydride can include succinic anhydride, maleic anhydride, N,N,N',N'-ethylenediaminetetraacetate dianhydride, phthalic anhydride, mellitic anhydride, pyromellitic anhydride, or a mixture thereof. In an exemplary embodiment, the acid halide can include adipoyl chloride, glutaryl chloride, sebacoyl chloride, or a mixture thereof.

In an exemplary embodiment, the polyamidoamine can have a molar ratio of polyalkylene polyamine to dicarboxylic acid of about 2:1 to 0.5:1, about 1.8:1 to 0.75:1, or about 1.6:1 to 085:1.

In an exemplary embodiment, the polyamidoamine resin can have a reduced specific viscosity of about 0.02 dL/g to 0.25 dL/g, about 0.04 dL/g to 0.20 dL/g, or about 0.06 dL/g to 0.18 dL/g. Reduced specific viscosity (RSV) can be measured using a glass capillary viscometer at 30° C. The efflux time of each sample can be determined three times and the average efflux time calculated. The RSV can be calculated using the following formula (1):

$$RSV=((t-t_0))/(t_0 c) \quad (1)$$

where t is the average efflux time of the polyamidoamine sample diluted with 1 M NaCl solution, $t_0$ is the average efflux time of 1 M NaCl solution, c is the concentration of the diluted polyamidoamine sample, which is 5 g/dL.

In an exemplary embodiment, the epihalohydrin can be a difunctional crosslinker that is used to prepare the polyamine polyamidoamine epihalohydrin resin. In an exemplary embodiment, the epihalohydrin can include epichlorohydrin, epifluorohydrin, epibromohydrin, or epiiodohydrin, alkyl-substituted epihalohydrins, or a mixture thereof. In an exemplary embodiment, the difunctional crosslinker for preparing the polyamine polyamindoamine epihalohydrin resin is epichlorohydrin.

In an exemplary embodiment, the PPAE resin can generally be formed by reacting polyamine, polyamidoamine, and epihalohydrin, in an aqueous medium.

In an exemplary embodiment, the weight ratio of polyamine to polyamidoamine, can be about 1:100 to 100:1, about 1:50 to 50:1, or about 1:20 to 20:1. In an exemplary embodiment, the reaction temperature can be about 25 to 100° C., about 40 to 90° C., or about 50 to 80° C.

In an exemplary embodiment, the total solids of the PPAE resin can be about 5 to 80%, about 10 to 50%, or about 15 to 30%. In an exemplary embodiment, the pH values of the PPAE resin can be about 2 to 10, about 3 to 9, or about 3 to 8. In an exemplary embodiment, the weight average molecular weight of the PPAE resin can be about 350 Daltons (Da) to 10 million Da, about 1000 Da to 5 million Da, or about 5000 Da to 3 million Da. In an exemplary embodiment, the Brookfield viscosity of the PPAE resin can be about 3 to 1000 cps, about 5 to 500 cps, or about 8 to 300 cps, for a 20% by weight aqueous solution.

In an exemplary embodiment, the PPAE resin has an epihalohydrin/amine (also expressed herein as "epi/amine" or "E/N") ratio of about 0.8 or less, about 0.5 or less, about 0.45 or less, about 0.4 or less, or about 0.3 or less. The epi/amine ratio is calculated as the molar ratio of epichlorohydrin content to amine content. In an embodiment, the PPAE resin has an E/N ratio of about 0.01 to 0.8, about 0.01 to 0.5, about 0.01 to 0.45, about 0.01 to 0.4, or about 0.01 to 0.3.

B2c) Aldehyde-Functionalized Polymer

In an exemplary embodiment, the aldehyde-functionalized polymer resin can be produced by reacting a polymer including one or more hydroxyl, amine, or amide groups with one or more aldehydes. In an exemplary embodiment, the polymeric aldehyde-functionalized polymer resin can comprise gloxylated polyacrylamides, aldehyde-rich cellulose, aldehyde-functional polysaccharides, or aldehyde functional cationic, anionic or non-ionic starches. Exemplary materials include those disclosed in U.S. Pat. No. 4,129,722, which is herein incorporated by reference. An example of a commercially available soluble cationic aldehyde functional starch is Cobond® 1000 marketed by National Starch. Additional exemplary aldehyde-functionalized polymers may include aldehyde polymers such as those disclosed in U.S. Pat. Nos. 5,085,736; 6,274,667; and 6,224,714; all of which are herein incorporated by reference, as well the those of WO 00/43428 and the aldehyde functional cellulose described in WO 00/50462 A1 and WO 01/34903 A1. In an exemplary embodiment, the polymeric aldehyde-functional resins can have a molecular weight of about 10,000 Da or greater, about 100,000 Da or greater, or about 500,000 Da or greater. Alternatively, the polymeric aldehyde-functionalized resins can have a molecular weight below about 200,000 Da, such as below about 60,000 Da.

In an exemplary embodiment, further examples of aldehyde-functionalized polymers can include dialdehyde guar, aldehyde-functional wet strength additives further comprising carboxylic groups as disclosed in WO 01/83887, dialdehyde inulin, and the dialdehyde-modified anionic and amphoteric polyacrylamides of WO 00/11046, each of which are herein incorporated by reference. Another exemplary aldehyde-functionalized polymer is an aldehyde-containing surfactant such as those disclosed in U.S. Pat. No. 6,306,249, which is incorporated herein by reference.

When used in an exemplary embodiment, the aldehyde-functionalized polymer can have at least about 5 milliequivalents (meq) of aldehyde per 100 grams of polymer, more specifically at least about 10 meq, more specifically about 20 meq or greater, or most specifically about 25 meq, per 100 grams of polymer or greater.

In an exemplary embodiment, the polymeric aldehyde-functionalized polymer can be a glyoxylated polyacrylamide, such as a cationic glyoxylated polyacrylamide as described in U.S. Pat. Nos. 3,556,932, 3,556,933, 4,605,702, 7,828,934, and U.S. Patent Application 20080308242, each of which is incorporated herein by reference. Such compounds include FENNOBOND™ 3000 and PAREZ™ 745 from Kemira Oyj of Helsinki, Finland, HERCOBOND™ 1366, manufactured by Hercules, Inc. of Wilmington, Del.

In an exemplary embodiment, the aldehyde functionalized polymer is a glyoxalated polyacrylamide resin having the ratio of the number of substituted glyoxal groups to the number of glyoxal-reactive amide groups being in excess of about 0.03:1, being in excess of about 0.10:1, or being in excess of about 0.15:1.

In an exemplary embodiment, the aldehyde functionalized polymer can be a glyoxalated polyacrylamide resin having a polyacrylamide backbone with a molar ratio of acrylamide to dimethyldiallylammonium chloride of about 99:1 to 50:50, about 98:1 to 60:40, or about 96:1 to 75:25. In an exemplary embodiment, the weight average molecular weight of the polyacrylamide backbone can be about 250,000 Da or less, about 150,000 Da or less, or about 100,000 Da or less. The Brookfield viscosity of the polyacrylamide backbone can be about 10 to 10,000 cps, about 25 to 5000 cps, about 50 to 2000 cps, for a 40% by weight aqueous solution.

B2d) Polyamidoamine Crosslinked with Dichloroethane

In an exemplary embodiment, the polyamidoamine crosslinked with dichloroethane resin can be prepared by reacting one or more polyalkylene polyamines and one or more dicarboxylic acid compounds to form a polyamidoamine and then reacting the polyamidoamine with dichloroethane to form the polyamidoamine crosslinked with dichloroethane resin (See, e.g., U.S. Pat. No. 6,303,002, which is incorporated herein by reference).

B2e) Polyvinylamine

In general, a suitable polyvinylamine may be used in the present disclosure. In an exemplary embodiment, the polyvinylamine polymer can be a homopolymer or can be a vinylamine-containing copolymer. In an exemplary embodiment, the polyvinylamine can have a molecular weight of about 1000 Da to 20 million Da or about 5000 Da to 2 million Da.

B2f) Polyvinylformamide/vinyl amine

In general, a suitable polyvinylformamide/vinyl amine may be used in the present disclosure. In an exemplary embodiment, the polyvinylformamide/vinyl amine can have a molecular weight of about 1000 Da to 20 million Da, or about 5000 Da to 2 million Da.

C) PPAE and Polymer Blend

In an exemplary embodiment, the applied absorbent material an include PPAE and the polymer blend. In an exemplary embodiment, the ratio of the PPAE to the polymer blend can be about 100:1 and 1:100.

D) Applied Absorbent Material Forming System

In an exemplary embodiment, the applied absorbent material forming system (e.g., PPAE, polymer blend, or a combination thereof) may be provided to a cellulosic fiber, which may be used to produce a paper product having an absorbent film. In an exemplary embodiment, the applied absorbent material forming system (or a component thereof) can be applied as a dried composition to a cellulosic web or individual fibers to form the applied absorbent material using techniques such as addition to a fiber slurry, wet sheet spraying, dry sheet spraying, powder application, rotogravure roll applications, extrusion application techniques, impregnation techniques, a combination thereof, or the like.

In an exemplary embodiment of the applied absorbent material forming system including the polymer blend or polymer blend and PPAE, the individual components of the applied absorbent material forming system may be combined first and then applied to a web or fibers, or the components may be applied sequentially in either order. After the components have been applied to the web, the web or fibers are dried and heatedly sufficiently to achieve the desired interaction between the two compounds.

By way of example only, application of the applied absorbent material forming system (or a component thereof) can be applied by any of the following methods or combinations thereof.

In an exemplary embodiment, the method can include direct addition of the applied absorbent material forming system (or a component thereof) to a fibrous slurry, such as by injection of the compound into a slurry prior to entry in the headbox. In an exemplary embodiment, the slurry can be about 0.001% to about 50%, about 0.2% to 10%, about 0.3% to about 5%, or about 0.4% to about 4%.

In an exemplary embodiment, the method can include spraying the applied absorbent material forming system (or a component thereof) to a fibrous web. For example, spray nozzles may be mounted over a moving paper web to apply a desired dose of a solution to a web that can be moist or substantially dry.

In an exemplary embodiment, the method can include application of the applied absorbent material forming system (or a component thereof) by spray or other means to a moving belt or fabric, which in turn contacts the tissue web to apply the chemical to the web, such as is disclosed in WO 01/49937.

In an exemplary embodiment, the method can include printing the applied absorbent material forming (or a component thereof) onto a web, such as by offset printing, gravure printing flexographic printing, ink jet printing, digital printing of any kind, and the like.

In an exemplary embodiment, the method can include coating the applied absorbent material forming system (or a component thereof) onto one or both surfaces of a web, such as blade coating, air knife coating, short dwell coating, cast coating, and the like.

In an exemplary embodiment, the method can include application of applied absorbent material forming system (or a component thereof) to individualized fibers. For example, comminuted or flash dried fibers may be entrained in an air stream combined with an aerosol or spray of the compound to treat individual fibers prior to incorporation into a web or other fibrous product.

In an exemplary embodiment, the method can include impregnation of a wet or dry web with the applied absorbent material forming system (or a component thereof), where the applied absorbent material forming system (or a component thereof) penetrates a significant distance into the thickness of the web, such as about 20% or more of the thickness of the web, about 30% or more of the thickness of the web, and about 70% or more of the thickness of the web, including completely penetrating the web throughout the full extent of its thickness.

In an exemplary embodiment, the method can include forming the applied absorbent material as described herein, drying the applied absorbent material, washing the soluble component from the applied absorbent material, re-drying the applied absorbent material, breaking the applied absorbent material into a powder, and applying the broken pieces to a structure, such as a paper sheet, so that the pieces attach to the structure.

When applied to the surface of a paper web, an exemplary embodiment of the present disclosure may include the topical application of the applied absorbent material forming system can occur on an embryonic web prior to Yankee drying or through drying, and optionally after final vacuum dewatering has been applied.

In an exemplary embodiment, the application level of the applied absorbent material forming system can be about 0.05% to about 10% by weight relative to the dry mass of the web for any of the paper strength system. In exemplary embodiment, the application level can be about 0.05% to about 4%, or about 0.1% to about 2%. Higher and lower application levels are also within the scope of the embodiments. In some embodiments, for example, application levels of from about 5% to about 50% or higher can be considered.

In an exemplary embodiment, the applied absorbent material forming system when combined with the web or with cellulosic fibers can have any pH, though in many embodiments it is desired that the applied absorbent material system is in solution in contact with the web or with fibers have a pH below about 10, about 9, about 8 or about 7, such as about 2 to about 8, about 2 to about 7, about 3 to about 6, and about 3 to about 5.5. Alternatively, the pH range may be about 5 to about 9, about 5.5 to about 8.5, or about 6 to about 8. These pH values can apply to the PPAE polymer prior to contacting the web or fibers, or to a mixture of the applied absorbent material forming system in contact with the web or the fibers prior to drying.

In an exemplary embodiment, before the applied absorbent material forming system is applied to an existing web, such as a moist embryonic web, the solids level of the web may be about 10% or higher (i.e., the web comprises about 10 grams of dry solids and 90 grams of water, such as about any of the following solids levels or higher: about 12%, about 15%, about 18%, about 20%, about 25%, about 30%, about 35%, about 40%, about 45%, about 50%, about 60%, about 75%, about 80%, about 90%, about 95%, about 98%, and about 99%, with exemplary ranges of about 30% to about 100% or about 65% to about 90%).

Ignoring the presence of chemical compounds other than the applied absorbent material forming system and focusing on the distribution of the applied absorbent material forming system in the web, one skilled in the art will recognize that the applied absorbent material forming system (including components and/or derivatives thereof) can be distributed in a wide variety of ways. For example, the applied absorbent material forming system may be uniformly distributed, or present in a pattern in the web, or selectively present on one surface or in one layer of a multilayered web. In multilayered webs, the entire thickness of the paper web may be subjected to application of the applied absorbent material forming system and other chemical treatments described herein, or each individual layer may be independently treated or untreated with the applied absorbent material forming system and other chemical treatments of the present disclosure. In an exemplary embodiment, the applied absorbent material forming system is predominantly applied to one layer in a multilayer web.

In an exemplary embodiment, certain chemical distributions may occur in webs that are pattern densified, such as the webs disclosed in any of the following U.S. Pat. Nos. 4,514,345; 4,528,239; 5,098,522; 5,260,171; 5,275,700; 5,328,565; 5,334,289; 5,431,786; 5,496,624; 5,500,277; 5,514,523; 5,554,467; 5,566,724; 5,624,790; and 5,628,876, the disclosures of which are incorporated herein by reference to the extent that they are non-contradictory herewith.

In an exemplary embodiment, the applied absorbent material forming system or other chemicals can be selectively concentrated in the densified regions of the web (e.g., a densified network corresponding to regions of the web compressed by an imprinting fabric pressing the web against a Yankee dryer, where the densified network can provide good tensile strength to the three-dimensional web).

In an exemplary embodiment, the applied absorbent material forming system (or components or derivatives thereof) may also be present substantially uniformly in the web, or at least without a selective concentration in either the densified or undensified regions.

According to an exemplary method, the conditions (e.g., temperature of the pulp slurry, temperature of pre-mixing the components, time of pre-mixing the components, concentration of the paper solution, co-mixing of solids, and the like) of the cellulosic fiber and process can vary, as necessary or desired, depending on the particular paper product to be formed, characteristics of the paper product formed, and the like. In an embodiment, the process variables may be modified as necessary or desired, including, for example, the temperature of pre-mixing the components, the time of pre-mixing the components, and the concentration of the pulp slurry.

In various exemplary embodiments a paper may be formed by the treatment of a cellulosic fiber or an aqueous pulp slurry with a applied absorbent material forming system as described herein. The paper can be formed using one or more methods, including those described herein.

EXAMPLES

Now having described the embodiments, in general, the examples describe some additional embodiments. While embodiments are described in connection with the examples and the corresponding text and figures, there is no intent to limit embodiments of the disclosure to these descriptions. On the contrary, the intent is to cover all alternatives, modifications, and equivalents included within the spirit and scope of exemplary embodiments.

Test Methods:
Conventional Tests:
Film insolubility and rewettability were measured in a combined test. For each adhesive sample, an adhesive film of a fixed thickness was prepared in a beaker by drying at 90° C. for 1 hr followed by 4 hr drying at 110° C. The dry film was weighed (initial dry film weight), covered with distilled water and agitated in a shaker at room temperature. The undissolved solids were separated, weighed (wet film weight after agitation in water), dried and weighed again (dry film weight after solubilization). The Percent Insolubility and Rewet Ratio were calculated as follows:

Percent Insolubility=(Dry film weight after solubilization)/(Initial dry film weight)×100 Rewet Ratio=(Wet film weight after agitation in water)/(Dry film weight after solubilization)

Example

Preparation of Polyamidomines
Polyamidoamine was first prepared by a condensation reaction of an excess amount of diethylenetriamine with adipic acid. In particular, diethylenetriamine was added to a three neck flask. Adipic acid was then slowly added to the flask and the reaction mixture heated to 165-170° C. and maintained for a period of 5 hours. At the end of the reaction, the product was diluted with water to adjust the concentration to 60% and the temperature was lowered to room temperature. Table 1 shows the charge ratios of diethylenetriamine and adipic acid.

TABLE 1

Charge ratios of polyamidoamine

| Polyamidoamine | Diethylenetriamine/adipic acid molar ratio |
|---|---|
| 1 | 1.6 |
| 2 | 1.0 |

Preparation of PPAE Resins

Polyamidoamine 1, diethylenetriamine, and water were first added to a one liter reactor with reflux. The weight ratio of diethylenetriamine to polyamidoamine was 0.07. The reactor was heated to 70° C. and maintained at this temperature throughout the reaction. Epichlorohydrin was then added to the reactor slowly to increase product viscosity. Water was added stepwise during the reaction to reduce viscosity buildup rate to avoid product gelation. Once the product reached the desired viscosity range, final charge of water was added to the reactor and pH was adjusted to around 5.0 using concentrated sulfuric acid (95%). The total concentration of the product was around 15% and the final viscosity was around 80 cps (Brookfield at 23° C.).

Preparation of PAE Resins

Polyamidoamine 2 and water were added to a one liter reactor with reflux. The reactor was heated to 70° C. and maintained at this temperature throughout the reaction. Epichlorohydrin was then added to the reactor in one shot. Once the product reached the desired viscosity range, final charge of water was added to the reactor and pH was adjusted to around 5.0 using concentrated sulfuric acid (95%). Table 2 shows the properties of two final products.

TABLE 2

Properties of PAE resins

| PAE | Concentration (wt %) | pH | Brookfield viscosity at 23° C. (cP) |
|---|---|---|---|
| 1 (680CA) | 25% | 4.0 | 45 |
| 2 (681AM+) | 15% | 4.0 | 55 |

Rewet and Insolubility Test Results

TABLE 3

Comparison of insolubility and rewet ratio for PPAE films vs. various conventional PAE films.

| Product | % Insolubility | Rewet ratio (based on initial dry film weight) | Rewet ratio (based on insoluble dry film weight) |
|---|---|---|---|
| PAE 1 | 0 | n/a | n/a |
| PAEPAEPAE 2 | 69 | 11 | 16 |
| PPAE | 58 | 20 | 34 |

PAE 1 at 100% is fully soluble and no rewet measurement is possible

Blends of Two PAE Polymers

Table 4 demonstrates that blending two PAE resins, exemplified by two creping adhesives, can dramatically improve rewet ratio. The best ratio is 24:1 for the 25/75 blend of PAE 2 and PAE 1. If this ratio is recalculated based on the insoluble fraction, the ratio increases to 53:1. This example also shows that rewet ratio and insolubility can be optimized to the desired levels by changing the ratio of two polymers.

TABLE 4

Insolubility and rewet ratio of blends of two PAE resins

| PAE 2/PAE 1 ratio (dry solids basis) | % Insolubility | Rewet ratio (based on initial dry film weight) | Rewet ratio (based on insoluble dry film weight) |
|---|---|---|---|
| 100/0 | 69 | 11 | 16 |
| 75/25 | 62 | 14 | 22 |
| 50/50 | 54 | 16 | 30 |
| 25/75 | 45 | 24 | 53 |
| 0/100 | 0 | n/a* | n/a* |

*PAE 1 film is fully soluble and no rewet measurement is possible

Blends of PAE and a Non-PAE Polymer

Table 5 demonstrates that blending PAE with a non-PAE polymer can improve rewet ratio. Again, optimal ratio can be achieved to provide minimal insolubility and high rewet ratio.

TABLE 5

Insolubility and rewet ratio for blends of PAE 1 with a non-PAE polymer, either a polyethyleneimine (PEI) resin or a polyamidoamine dichloroethane (PAD) resin. The PEI resin was a reaction product of polyalkylene polyamine and dichloroethane with a final viscosity of 170 cps at 25% concentration in water. The PAD resin was a reaction product between polyamidoamine and dichloroethane with a final viscosity of 110 cps at 29% concentration in water.

| PAE 2/another polymer ratio (dry solids basis) | % Insolubility | | Rewet Ratio (based on initial solids) | | Rewet Ratio (based on insoluble fraction) | |
|---|---|---|---|---|---|---|
| | PEI | PAD | PEI | PAD | PEI | PAD |
| 100/0 | 65 | 65 | 10 | 10 | 16 | 16 |
| 75/25 | 61 | 61 | 10 | 10 | 16 | 16 |
| 50/50 | 44 | 47 | 17 | 13 | 38 | 27 |
| 25/75 | 15 | 25 | 9 | 15 | 59 | 59 |
| 0/100 | 0 | 0 | n/a* | n/a* | n/a* | n/a* |

*Another polymer film is fully soluble and no rewet measurement is possible

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

We claim:

1. A non-creped absorbent structure comprising a fiber treated with a system forming an applied absorbent material, said system comprising a polyamine polyamidoamine epihalohydrin resin and a blend of two or more polymers, wherein at least one first polymer is self-crosslinking and reactive towards one of the other polymers in the blend, and at least a second polymer that reacts with the first polymer, wherein the polyamine polyamidoamine epihalohydrin resin is the reaction product of a polyamidoamine, a first polyamine, and an epihalohydrin, wherein the reaction product is formed by reacting the polyamidoamine, the first polyamine, and the epihalohydrin in an aqueous medium.

2. The structure of claim 1, wherein the polyamine polyamidoamine epihalohydrin resin has a total AOX level of 400 ppm or less.

3. The structure of claim 1, wherein the polyamidoamine is prepared by a process comprising reacting a polycarboxylic acid, a polycarboxylic acid derivative, or a combination thereof with a second polyamine to form the polyamidoamine, wherein a molar ratio of the second polyamine to the polycarboxylic acid, polycarboxylic acid derivative, or combination thereof, is 1.05 to 2.0.

4. The structure of claim 3, wherein the polycarboxylic acid and the polycarboxylic acid derivative are independently selected from the group consisting of: malonic acid, glutaric acid, adipic acid, azelaic acid, citric acid, tricarballylic acid (1,2,3-propanetricarboxylic acid), 1,2,3,4 butanetetracarboxylic acid, nitrilotriacetic acid, N,N,N',N'-ethylenediaminetetraacetate, 1,2-cyclohexanedicarboxylic acid, 1,3-cyclohexanedicarboxylic acid, 1,4-cyclohexanedicarboxylic acid, itaconic acid, phthalic acid, isophthalic acid, terephthalic acid, 1,2,4-benzenetricarboxylic acid (trimellitic acid) and 1,2,4,5-benzenetetracarboxylic acid (pyromellitic acid), dimethyl adipate, dimethyl malonate, diethyl malonate, dimethyl succinate, dimethyl glutarate, diethyl glutarate, succinic anhydride, maleic anhydride, N,N,N',N'-ethylenediaminetetraacetate dianhydride, phthalic anhydride, mellitic anhydride, pyromellitic anhydride, adipoyl chloride, glutaryl chloride, sebacoyl chloride, and a mixture thereof.

5. The structure of claim 3, wherein the polyamine polyamidoamine epihalohydrin resin has a weight average molecular weight of 350 Daltons (Da) to 10 million Da.

6. The structure of claim 3, wherein the first polyamine and the second polyamine are independently selected from the group consisting of: ammonium, urea, aliphatic amines, aromatic amines, ethylenediamine (EDA), diethylenetriamine (DETA), triethylenetetramine (TETA), tetraethylenepentamine (TEPA), dipropylenetriamine (DPTA), bishexamethylenetriamine (BHMT), N-methylbis(aminopropyl)amine (MBAPA), aminoethylpiperazine (AEP), pentaethylenehexamine (PEHA), and a mixture thereof.

7. The structure of claim 3, wherein the weight ratio of the first polyamine to the polyamidoamine is 1:20 to 20:1.

8. The structure of claim 1, wherein the applied absorbent material has a thickness of 0.001 micrometers to 1000 micrometers.

9. The structure of claim 1, wherein the first polymer is selected from the group consisting of: a cross-linking PAE, a cross-linking PPAE, and a cross-linking aldehyde-functionalized polymer resin.

10. The structure of claim 9, wherein the weight ratio of aldehyde-functionalized polymer resin to polyamine polyamidoamine epihalohydrin resin is 1:1 to 100:1.

11. The structure of claim 1, wherein the second polymer is selected from the group consisting of: a PAE, a PPAE, an aldehyde-functionalized polymer resin, a polyamidoamine cross-linked with dichloroethan, a polyvinylamine, a polyvinylformamide/vinyl amine, a polyamidoamine, a polyethyleneimine, and a polymer that is reactive to an aldehyde, wherein the polymer that is reactive to aldehyde is selected from the group consisting of: a polyacrylamide, a starch or its derivatives, a carboxymethylcellulose, and a polyvinyl alcohol.

12. The structure of claim 1, wherein the ratio of the first polymer to the second polymer is 10:90 to 90:10.

13. The structure of claim 1, wherein the absorbent structure is in the form of a paper material or a nonwoven fabric or web.

14. The structure of claim 1, wherein the absorbent structure including the applied absorbent material is a paper product that is selected from the group consisting of: a paper towel, a napkin, a tissue, an absorbent pad, a diaper, a feminine hygiene product, and a sanitary napkin.

15. A method of making the absorbent structure of claim 1, comprising: introducing to a fiber an applied absorbent material forming system comprising a polyamine polyamidoamine epihalohydrin resin and a blend of two or more polymers, wherein at least one first polymer is self-crosslinking and reactive towards one of the other polymers in the blend, and at least a second polymer that reacts with the first polymer.

16. The method of claim 15, further comprising: forming the applied absorbent material on the absorbent structure.

* * * * *